Figure 1:
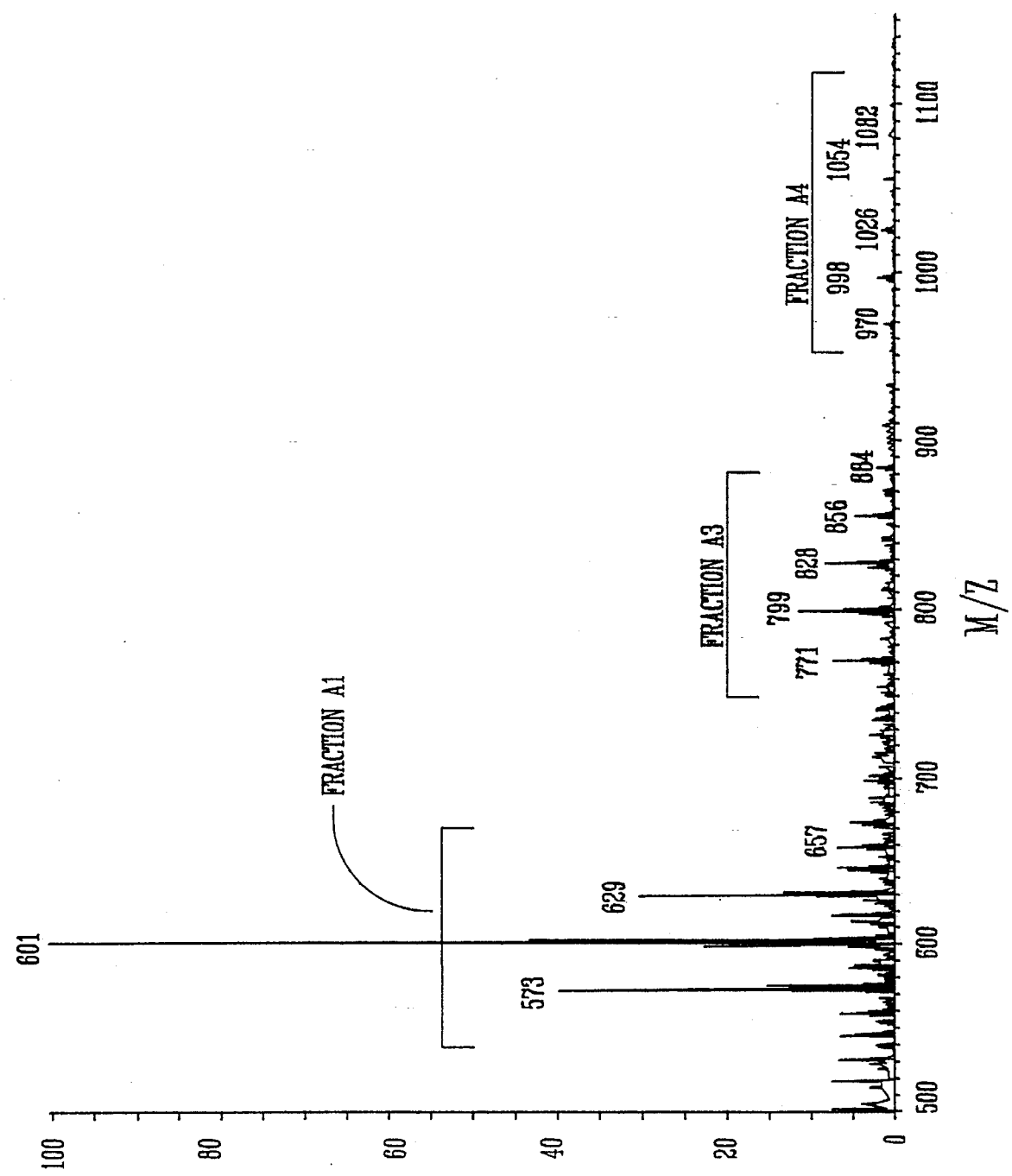

US005607971A

United States Patent [19]
Al-Mahmoud et al.

[11] Patent Number: 5,607,971
[45] Date of Patent: Mar. 4, 1997

[54] ESTERIFIED VASOACTIVE LIPIDS FOR INCREASING PERFUSION PRESSURE OF THE CARUNCULAR ARTERIAL BED IN MAMMALS

[75] Inventors: Mohsen Al-Mahmoud, Irbid, Jordan; Stephen P. Ford, Huxley, Iowa; Robert E. Short, Miles City, Mont.; Donna B. Farley, North Liberty, Iowa; Lane Christenson, Urbandale, Iowa; John P. N. Rossaza, Iowa City, Iowa

[73] Assignees: University of Iowa Research Foundation, Iowa City, Iowa; Iowa State University Research Foundation, Inc., Ames, Iowa; The United States of America as represented by the Secretary of Agriculture, Washington, D.C.

[21] Appl. No.: 413,797

[22] Filed: Jun. 19, 1995

[51] Int. Cl.$^6$ ..................................... A61K 31/23
[52] U.S. Cl. .................... 514/552; 554/227; 424/196.1
[58] Field of Search .................... 514/552; 424/196.1

[56] References Cited

U.S. PATENT DOCUMENTS

| | | | |
|---|---|---|---|
| 4,046,914 | 9/1977 | Hallgren et al. | 514/552 |
| 4,329,359 | 5/1982 | Stahly | 514/552 |
| 5,306,729 | 4/1994 | Spiegelman et al. | 514/552 |
| 5,444,089 | 8/1995 | Li et al. | 514/552 |
| 5,466,453 | 11/1995 | Uchida et al. | 424/196.1 |

OTHER PUBLICATIONS

Kalviainen et al., *Age-related contents of polymerized lipids in the ectohydric forest mosses Pleurozium schreberi and Hylocomium splendens*, Physiol. Plant 65:269–273 Copenhagen 1985.
Short et al., *Effects of Feeding Ponderosa Pine Needles During Pregnancy: Comparative Studies with Bison, Cattle, Goats and Sheep*, J. Anim. Sci. 1992, 70:3498–3504.
Jensen et al., *Mass spectrometry methods for structural determination and analysis of fatty acids*, Mass Spectrometry Review 1987, 6, 497–536.
Chow et al., *Reproductive Failure of Mice Caused by Pine Needle Ingestion*, J. Reprod. Fert. (1972) 30, 169–172.
Anderson et al., *Embryotoxic Effects of Pine Needles and Pine Needle Extracts*, Cornell Vet. 1979, 69: 169–175.
Anderson et al., *Pine Needle Toxicity in Pregnant Mice*, Cornell Vet., 1977, 67: 229–235.
Sharkawy et al., *Microbial Oxidation of Oleic Acid*, Applied & Env. Microbiology, Jul. 1992, pp. 2116–2122.
Fuji et al., *Minor Components of Ponderosa Pine Oleoresin*, Biochemistry, vol. 23, No. 4 pp. 875–878, 1984.
Hu et al., *Substituted Fatty Acids in the Leaves of Some Higher Plants*, LIPIDS, vol. 23, No. 7 (1988).
Lacy et al., *Ponderosa Pine: Economic Impact*, Westview Special Studies in Agriculture Science and Policy, pp. 95–106 (1990).
James et al., *Effect of Feeding Ponderosa Pine Needle Extracts and Their Residues to Pregnant Cattle*, Cornell Vet. 1994:84:33–39.
Zinkel et al., *Resin Acids of Pinus Ponderosa Needles*, Phytochemistry vol. 30 No. 3, pp. 845–848, 1991.
Kubik et al., *Embryo Resorptions in Mice Induced by Diterpene Resin Acids of Pinus Ponderosa Needles*, Cornell Vet. 1981, 71:34–42.
James et al., *Pine Needle Abortion in Cattle: A Review and Report of 1973–1984 Research*, Cornell Vet. 1989, 79:39–52.
Allison et al., *Further Studies on the Anti-Estrogen Activity of Yellow Pine Needles*, Univ. of British Columbia, pp. 1155–1159 (Oct. 1990).
Panter et al., *Premature Bovine Parturition Induced by Ponderosa Pine: Effects of Pine Needles, Bark and Branch Tips*, Cornell Vet. 1990;80:No. 4 pp. 329–338.
Ford et al., *Effects of Ponderosa Pine Needle Ingestion on Uterine Vascular Function in Late-Gestation Beef Cows*, J. Anim. Sci. 1992, 70:1609–1614.
Franch et al., *Constituent Acids of Pinus Radiata Stem Cutin*, Phytochemistry vol. 21, No. 11 pp. 2687–2689, 1982.
Makowski et al., *Distribution of uterine blood flow in the pregnant sheep*, Am. J. Obst. & Gyn. June?, pp. 409–412 (1994).
Stuart et al., *Pine Needle Abortion in Cattle Pathological Observations*, Cornell Vet. 1989, 79:61–69.
Christenson et al., *Effects of ingestion of pine needles (Pinus ponderosa) by late-pregnant beef cows on potential sensitive Ca2+channel activity of caruncular arteries*, J. Reprod. and Fertility (1993) 98, 301–306.
Gardner et al., *Ponderosa Pine Needle-Induced Abortion in Beef Cattle: Identification of Iscupressic Acid as the Principal Active Compound*, J. Agric. Food Chem. 1994, 42, 756–761.
Eglinton et al., *Gas Chromatographic-Mass Spectrometric Studies of Long Chain Hydroxy Acids.-III*, Organic Mass Spectrometry, 1968, vol. 1 pp. 591 to 611, Northern Ireland.
Adams, *Charge-remote fragmentations: Analytical applications and fundamental studies*, Mass Spectrometry Reviews 1990, 9, 141–186.

Primary Examiner—James H. Reamer
Attorney, Agent, or Firm—Zarley, McKee, Thomte, Voorhees, & Sease

[57] ABSTRACT

Esterified alkanediols which increase perfusion pressure of the caruncular arterial bed in mammals.

11 Claims, 9 Drawing Sheets

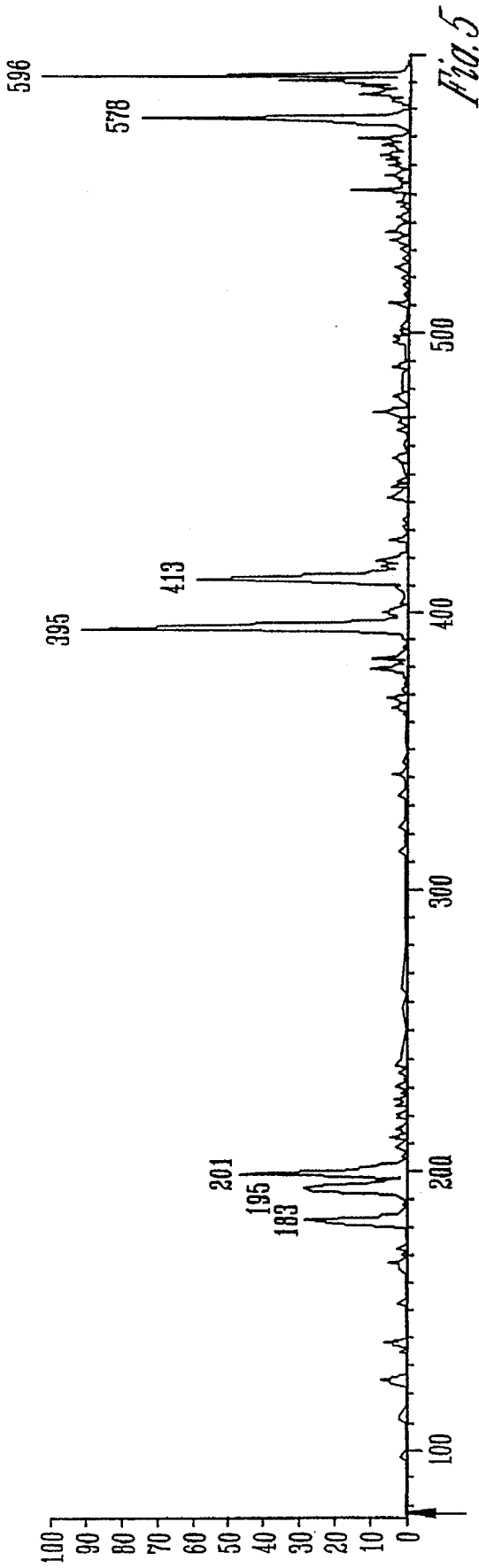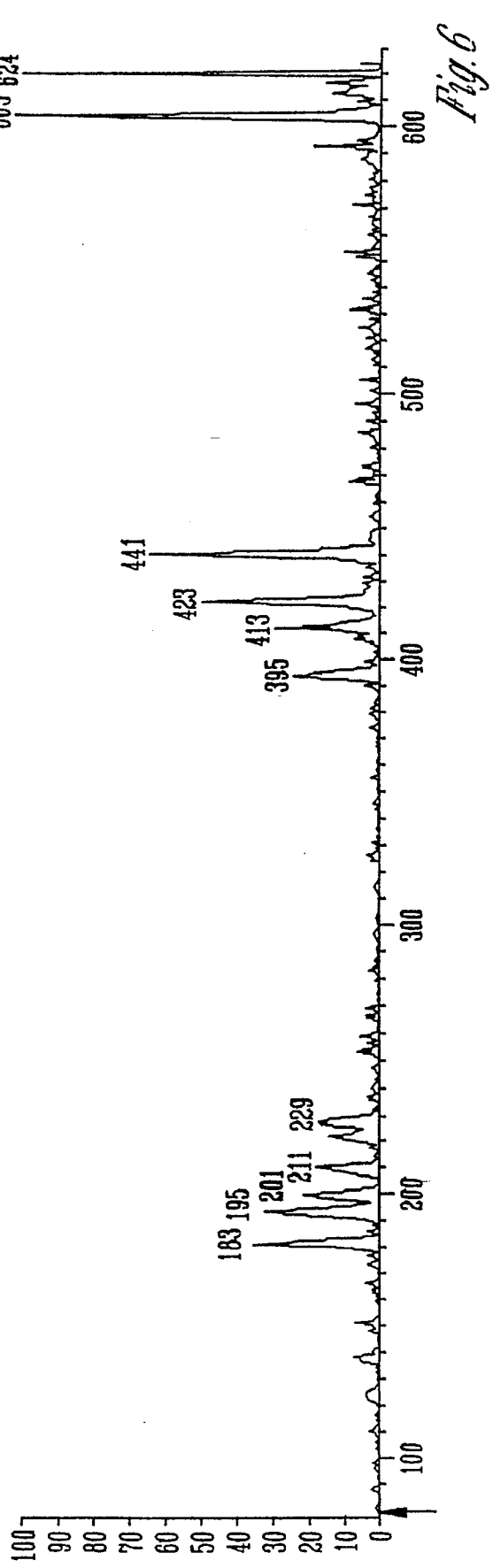

Fig. 8

- HEXADECANE-1,16-DIOL-1-O-TMS
- TETRADECANE-1,14-di-O-TMS

TIME (MIN)

Fig. 7

- METHYL MYRISTATE
- METHYL LAURATE
- METHYL PALMITATE
- TETRADECANE-1,14-di-O-TMS
- HEXADECANE-1,16-DIOL-1-O-TMS

TIME (MIN)

ESTERIFIED VASOACTIVE LIPIDS FOR INCREASING PERFUSION PRESSURE OF THE CARUNCULAR ARTERIAL BED IN MAMMALS

GRANT REFERENCE CLAUSE

Work for this invention was funded in part by a grant from United States Department of Agriculture, Agricultural Research Grant #8901729. The Government may have certain rights in this invention.

FIELD OF THE INVENTION

The present invention relates to methods of inducing physiological effects in animals, in particular, a method for decreasing perfusion of blood through the caruncular arterial bed in mammals.

BACKGROUND OF THE INVENTION

*Pinus ponderosa,* or western yellow pine (Pinaceae) is abundant in western and midwestern states and in western Canada. Needles from *P. ponderosa* cause cattle to abort if they are consumed during late gestation (McDonald, *Veterinary Endocrinology and Reproduction* 1969; Stevenson et al., Pine Needle (*Pinus ponderosa*)-Induced Abortion in Range Cattle, *Cornell Vet.,* pp. 519–524, 1972). *P. ponderosa* ingestion induces premature parturition in cattle by causing prolonged vasoconstriction (i.e. increased vascular tone) of the caruncular arterial bed partially through increases in potential sensitive calcium channel (PSC) activity (Christenson et al., Effects of Pine Needles (*Pinus ponderosa*) by Late-Pregnant Beef Cows on Potential Sensitive $Ca^{2+}$ Channel Activity of Caruncular Arteries, *J. Reprod. Fertil.* pp. 301–306, 1993) resulting in a decrease in uterine blood flow.

In pregnancy, blood flow to the gravid bovine uterus increases ≈40 fold from conception to term (Ferrell and Ford, Blood Flow, Steroid Secretion and Nutrient Uptake of the Gravid Bovine Uterus, *J. Anim. Sci.,* 50, p. 1113–1121, 1980). After day 200, 80–85% of the uterine arterial blood flows through the caruncular arterial bed (Macowski et al., Distribution of Uterine Blood Flow in the Pregnant Sheep, *Am. J. Obstet. Gynecol,* 101 pp. 409–412, 1968) as a consequence of marked decreases in caruncular arterial tone (Ford, Control of Blood Flow to the Gravid Uterus of Domestic Livestock Species, *J. Anim. Sci.,* pp. 32–43, 1994). Early calving following pine needle consumption is accompanied by a profound constriction of caruncular arteries and ischemic necrosis at the placental attachment site (Stuart, et al., Pine Needle abortion in cattle: Pathological observations, *Cornell Vet.* 79, pp. 61–69, 1989). It is believed that components in pine needles increase the tone of the caruncular artery, resulting in a reduction of blood flow to the fetal-maternal interface.

Decreases in uterine arterial blood flow appear to result from activation of α2-adrenergic receptors on the vascular smooth muscle membrane of the artery (Ford et al., Effects of Ponderosa pine needle ingestion on uterine vascular function in late-gestation beef cows, *J. Anim. Sci.,* 70, pp. 1609–1614, 1992). Specifically, α2 activation facilitates extracellular uptake of calcium via PSC resulting in decreased vessel diameter (i.e. increased vessel tone) and uterine blood flow.

*Pinus ponderosa* is the only known species of Pinus to cause abortion in cattle in the United States and Canada (Pammel, Manual of Poisonous Plants, The Torch Press p. 330, 1911; James et al., Pine Needle Abortion in Cattle: A Review and Report of Recent Research, *Cornell Vet.,* pp. 39–52, 1989; Allison and Kitts, Further studies on the anti-estrogenic activity of yellow pine needles, *J. Anim. Sci.,* pp. 1155–1159, 1964). This results in large economic losses each year to the beef industry in the western United States (Lacey et al., Ponderosa Pine: Economic Impact In: The ecology and economic impact of poisonous plants on livestock production, pp. 95–106, 1988).

Both green and dry needles appear to cause abortion (Jensen et al., Evaluation of Histopathologic and Physiologic Changes in Cows Having Premature Births After Consuming Ponderosa Pine Needles, *Am. J. Vet. Res.* pp. 285–289, 1989), and bark and branch tips appear to contain abortifacient principles (Panter et al., Premature Bovine Parturition Induced by Ponderosa Pine: Effects of Pine Needles, Bark, and Branch Tips, *Cornell Vet.,* pp. 329–338, 1990). The nature of the abortifacient principles of ponderosa pine needles has been sought for nearly forty years. Many test animals or organ assays have been used to suggest a number of substances ranging from luteolytic agents like the prostaglandins to mycotoxins or the presence of infectious microorganisms (James et al., Pine Needle Abortion in Cattle: A Review and Report of Recent Research, *Cornell Vet.* 79, pp. 39–52 1989).

James and coworkers recently reported that pine needles extracted with selected solvents lost their ability to induce parturition when fed to pregnant cows (James et al., Effects of Feeding Ponderosa Pine Needle Extracts and Their Residues to Pregnant Cattle, *Cornell Vet.* pp. 33–39, 1994). The diterpene known as isocupressic acid was previously isolated from *P. ponderosa* (Zinkel and Magee, Resin Acids of *Pinus ponderosa* Needles, *Phytochemistry,* pp. 845–848, 1991), and diterpene resins have been implicated in embryotoxic effects in mice (Kubic and Jackson, Embryo Resorption in Mice Induced by Diterpine Resin Acids of *Pinus ponderosa* Needles, *Cornell Vet.* pp. 34–42, 1981).

James et al., found that an 80% pure sample of isocupressic acid isolated from *P. ponderosa* needles and bark induced early parturition in pregnant cattle (Gardner et al., Ponderosa Pine Needle-Induced Abortion in Beef Cattle: Identification of Isocupressic Acid as the Principle Active Compound. *J. Agric. Food Chem.* pp. 756–761, 1994) thus identifying one abortifacient principle in ponderosa pine needles. To date, isocupressic acid is the only compound that has been isolated and successfully shown to cause abortion in pregnant beef cattle.

Numerous classes of natural products have been isolated from *P. ponderosa* including volatile monoterpenes, sesquiterpenes, diterpenes, and wax alcohols and acids from chitin and suberin. It has now been discovered that the lipid diester component from *P. ponderosa* increases caruncular arterial tone partially through increasing PSC activity. These lipids may play a role in causing early parturition in pregnant beef cattle and may potentially be used to cause parturition in other mammals as well.

Accordingly, it is a primary objective of the present invention to provide a process for preparing novel vasoactive lipid substances which induce parturition in mammals.

Another primary objective of the present invention is to prepare a range of esterified fatty acids which can be investigated as drugs for the inducement of parturition.

A still further objective of the present invention is to provide a wide range of esterified fatty acids which can be systematically used and tested to determine structure-activity relationships for increasing caruncular arterial tone partially through increase in PSC activity.

SUMMARY OF THE INVENTION

Vasoactive lipid substances are provided which are isolated from *P. ponderosa* pine needles. The compounds cause an increase in caruncular arterial tone partially through increase in PSC activity, leading to compounds which may be used to induce parturition in mammals.

BRIEF DESCRIPTION OF THE DRAWINGS

FIG. 1 is the low resolution FAB-MS (Matrix 3NBA-Li) of *P. ponderosa* fraction F7(1–10) indicating mixtures of similar compounds.

FIG. 2 shows the 1H-NMR ($CDCl_3$) of fraction A-1 at 360 MHz.

FIG. 3 shows the 13C-NMR ($CDCl_3$) of fraction A1 at 90.5 MHz.

FIG. 4 shows the FAB MS spectrum (3NBA) of fraction A1.

FIG. 5 shows the metastable ion spectra of fraction A1 peak m/z596.

FIG. 6 shows the metastable ion spectra of fraction A1 peak m/z624.

FIG. 7 shows the GC total ion current chromatograMS of the neutral fraction obtained by saponification of fraction A1 and derivatization with BSTFA and $CH_3OH/BF_3$.

FIG. 8 shows the GC total ion current chromatograMS of the acidic fraction obtained by saponification of fraction A1 and derivatization with BSTFA and $CH_3OH/BF_3$.

FIG. 9 shows the 1H-NMR ($CDCl_3$) spectra of fraction A3 at 360 MHz.

FIG. 10 shows the 13C-NMR spectra of fraction A3 at 90.5 MHz.

FIG. 11 shows the FAB MS spectrum (3NBA) of fraction A3.

DETAILED DESCRIPTION OF THE PREFERRED EMBODIMENT

The focus of this application is on the isolation and uses of novel vasoactive esterified fatty acids which are selectively active at the uterine vasculature. Preferred compounds include esters of lauric, myristic and/or palmitic acids. The most preferred compounds are the aforementioned fatty acids esterified with alkanediols. The very most preferred compounds are esterified with 1,14-tetradecanedioyl and 1,16-hexadecanedioyl. These very most preferred compounds include:

1) 1,14-tetradecanedioyl-dilaurate;

2) 1,14-tetradecanedioyl-1-laurate-14-myristate;

3) 1,14 tetradecanedioyl-dimyristate 4) 1,16-hexadecanedioyl-laurate-myristate;

5) 1,14-tetradecanedioyl-laurate-palmitate;

Other suitable compounds include esters comprised of two fatty acids esterified together with one alkanediol and one ω-hydroxy fatty acid. These compounds have the following structures:

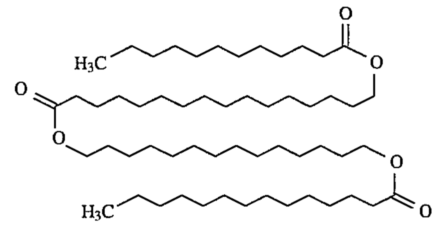

7

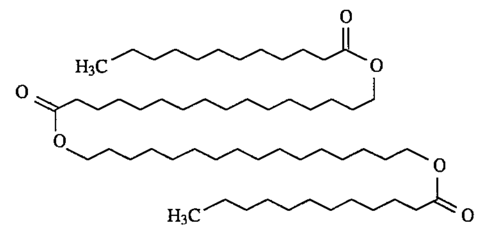

8

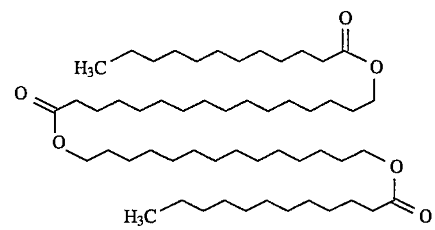

9

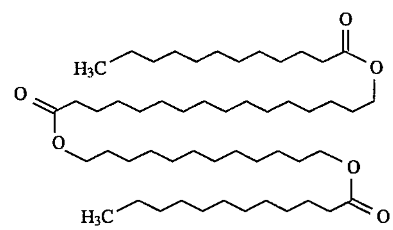

10

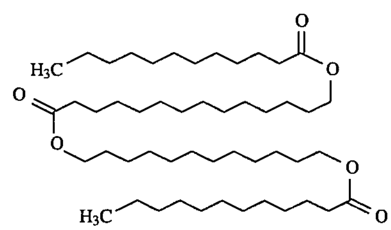

11

As previously stated, the parturition-inducing properties of *P. ponderosa* needles in cattle have been known for many years, but the component or components in the needles responsible for this effect were not. Isocupressic acid has been isolated and identified as an abortifacient component of *P. ponderosa,* but so far has been the only compound producing this effect which has thusfar been isolated.

Applicants have now successfully isolated a novel class of vasoactive compounds from *P. ponderosa* which have never been previously identified or isolated. Theoretically, these compounds would have their greatest effect on the uterine vasculature. During pregnancy, the caruncular arterial bed is preferentially dilated so that nutrients from the mother can more readily reach the fetus. Physiologically, the potential sensitive calcium channels of the caruncular arterial bed are closed to prevent the influx of calcium which would cause the blood vessels to constrict. Since blood vessels in the body normally have a high degree of calcium channel activity, a compound which would increase the influx of calcium would logically have its most dramatic effect on vasculature which is not normally experiencing this severely reduced calcium channel activity due to the state of pregnancy.

Preliminary observations conducted by Applicants have confirmed this theory. Based on tests conducted on cattle which have ingested ponderosa pine needles, the vasoactive compounds present in the needles appear to be selectively active for uterine vasculature. After eating the pine needles, the cattle showed no signs of increased systemic blood pressure or increases in heart rate, but exhibited marked and progressive decreases in uterine blood flow (Christenson et al., Effects of Ingestion of Ponderosa Pine Needles by Late-Pregnant Cows on Uterine Blood Flow and Steroid Secretion, *J. Anim. Sci.*, 70, pp. 531–537, 1992).

Such compounds offer many potential therapeutic uses in mammals. Ponderosa pine needles contain a variety of different mixed chemical components, some of which induce parturition, but many others which do not and as well may have the potential to produce unwanted side effects if ingested. Applicants have now identified the chemical structure and composition of several compounds present in the pine needles, which when isolated, purified, and/or synthesized, and fed to mammals produce beneficent and therapeutic results. Further, the possible adverse effects of the unknown mixed components of pine needles can be avoided.

In addition, due to the unique selectivity of these new compounds for uterine vasculature only, unwanted systemic vascular effects which often occur with vasoactive drugs can be avoided, such as increases in blood pressure and heart rate.

Potential uses of these new vasoactive compounds include, but are in no way limited to, treatment or prevention of postpartum hemorrhage, induction of labor, and inducement of parturition. Based on the tests conducted, a potential dosing plan for the inducement of in vivo parturition in mammals would be in the broad range of ½ to 1 milogram/kilogram of body weight/day, orally, for 8–10 days. The preferred dose would be 1 milogram/kilogram of body weight/day, orally, for 10 days.

The isolation of the lipid diesters was achieved by the general scheme shown below. Steam distillation, various Soxhlet extraction and acid and base partitionings of pine needle fractions were all examined during the process of developing the most useful protocol for isolating fractions containing vasoactive principles.

EXAMPLES

Chemicals

Lauric acid, myristic acid, palmitic acid, 10-hydroxydecanoic acid, methyl laurate, methyl myristate, methyl palmitate, dodecan-1-ol, 1,12-dodecanediol and 1,14-tetradecanediol were purchased from Aldrich Co., Milwaukee, Wis. The purities of each of these compounds and their identities were confirmed by chromatography (TLC, GC) and mass spectrometry before use.

Plant Material

*Pinus ponderosa* needles were collected in Custer County, Mont. in the Winter of 1989. A voucher specimen is deposited in the herbarium of the botany department, Montana State University, Bozeman, Mont.

General Experimental and Equipment

Melting points were recorded on Thomas Hoover Unimelt capillary melting point apparatus and are uncorrected. Infrared (IR) spectra were obtained using a Nicolet 205 FT-IR spectrometer connected with a Hewlett-Packard ColorPro plotter.

Chemical ionization mass spectral (CIMS) analyses were obtained using a Nermag R 1010c instrument. Fast atom bombardment (FAB) experiments were performed on a ZAB-HF reversed geometry (BE configuration, where B is a magnetic sector and E is an electrostatic analyzer) mass spectrometer (MS)(VG Analytic, Inc.). It is equipped with an Ion Tech saddle-field FAB gun and commercial FAB ion source. Samples were bombarded with 8 keV Xe atoMS at an atom gun current of 1.5 mA. 3-Nitrobenzyl alcohol (Aldrich) and magic bullet 5:1 dithiothreitol/dithioerythreitol (Sigma) were the FAB matrices used. Samples were dissolved in methylene chloride and then 1 µL was added to the matrix on the FAB probe tip (Adams, Analytical Applications and Fundamental Studies, *Mass Spectrom. Rev.*, pp. 141–186 1990; Jensen and Gross, 1987). Tandem mass spectrometry experiments (MS-MS) were also performed on the ZAB-HF MS. The technique of mass-analyzed ion kinetic energy spectrometry (MIKES) was used to detect the unimolecular ion decompositions in the region between B and E. A particular precursor ion was selected by the magnet and, by a scanning E, product ions that were formed by unimolecular ion decompositions in this region can be observed. The MS-MS spectra are the result of averaging eight to ten scans using VG software.

Nuclear magnetic resonance (NMR) spectra were obtained on Bruker NM-360 MHz and Varian NMR-500 MHz high field spectrometers equipped with an IBM Aspect-2000 processor and with a software VNMR version 4.1b, respectively. $^1$H-(360.134 and 499.843 MHz) and $^{13}$C-NMR (90.15 and 125.697 MHz) spectra were recorded using tetramethylsilane ($\delta$=0) or solvent peaks as internal standards.

Chromatography

Thin layer chromatography (TLC) was performed on 0.25 mm layers of silica gel GF254 (Merck) prepared on 5×20 cm or 20×20 cm glass plates with a Quikfit Industries spreader (London, UK). Plates were air dried and activated at 120° for a 1 hour prior to use. Plates were developed in a solvent mixture of $CH_2C_{12}/C_6H_{12}/CH_3CN$ (20:5:0.1, v/v/v), and developed chromatograms were visualized by spraying with a solution of $H_2SO_4$:EtOH (1:5 v/v) before warming with a heat gun to develop black spots. Flash column chromatography (FCC) was performed using JTBaker glassware with 40 mm silica gel (Baker) as the stationary absorbent phase. Solvent compositions similar to those described for TLC were used in the elution of samples from flash columns.

Pine Needle Fractionation

*P. ponderosa* pine needles were milled using a Fitzpatrick Model D. Hammer Mill (The Fitzpatrick Co., Elmhurst, Ill.) at medium speed with knives forward and fitted with a #8 mesh stainless steel screen.

For steam distillation, a total of 500 g of milled pine needles were suspended in 3L dist. $H_2O$ in a 5 L round bottom flask and refluxed to give 500 mL of distillate. Volatile oils were salted out with NaCl, and extracted with $CH_2C_{12}$ (3×250 ml). The organic extract was dried over anhydrous $Na_2SO_4$ and concentrated under vacuum to give 700 mg of volatile oil. The aqueous phase remaining after distillation was filtered, acidified to pH 2 with 6N HCl and extracted with $CH_2C_{12}$(3×500 ml). The organic extract was dried over anhydrous $Na_2SO_4$ and concentrated under reduced pressure to obtain 3.5 g of powder. The acidified aqueous mixture was further extracted with EtOAc/n-BuOH (9:1, v/v)(3×300 ml) to give after drying and concentrating, 3.5 g. Finally, the exhausted pine needles were macerated in 95% EtOH (1.5 L) for three days. The ethanolic suspension was filtered, the marc was discarded and the EtOH extract was evaporated under vacuum to five 38 g. These fractions were all insoluble in water and soluble in DMSO.

For Soxhlet extractions, 500 g of milled pine needles were exhaustively extracted in a Soxhlet apparatus with 2.5 L each of diethyl ether ($Et_2O$), methylene chloride ($CH_2Cl_2$) and methanol ($CH_3OH$). Extracts were filtered and concentrated under reduced pressure to give the following amounts of samples: $Et_2O$, 40 g; $CH_2C_{12}$, 12 g; and $CH_3OH$, 80 g (Scheme 1).

Chromatographic Fractionation of $CH_2Cl_2$ Extracts

An 8 g sample of the $CH_2Cl_2$ extract was loaded onto a $SiO_2$ flash column (4 cm×60 cm, 200 g, 40 µ mesh) and the column was eluted with 2 L each of $C_6H_{12}$; and mixtures of $C_6H_{12}+CH_2C_{12}$ and $CH_3OH$ of increasing polarities while fractions of 200 mL were collected. Similar fractions (TLC) were combined and concentrated. The largest sample (A) of 5.3 g was obtained by elution with 20% $C_6H_{12}$ in $CH_2Cl_2$. This sample (2 g) was further fractionated over a second $SiO_2$ flash column (2.5 cm×67 cm, 75 g, 40 µ mesh silica gel) and eluted with petroleum ether/$Et_2O$/HCOOH (50:50:0.8, v/v/v), while 10 ml fractions were collected. The fractions were monitored by TLC using $CHCl_3$/HCOOH (49:1, v/v) and $Et2O$/petroleum ether/HCOOH (50:50:0.8, v/v/v). Fractions 1–10 contained 227 mg of an apparently single spot by TLC at $R_f$ 0.72 with $CHCl_3$/HCOOH (49:1). However, with $CH_2Cl_2$/$C_6H_{12}$/$CH_3CN$ (20:5:0.1 v/v/v) as the solvent system, this fraction actually consisted of a separable mixture of three components of $R_f$ 0.25, 0.5 and 0.7.

A simpler chromatographic purification was achieved by adsorbing 1 g of $CH_2Cl_2$ extract onto 80 g of silica gel (40 µmesh) held in a 2.5 cm×60 cm column and eluting stepwise with 500 ml of hexane, mixtures of $CH_2Cl_2$/$C_6H_{12}$/$CH_3CN$ beginning with (20:20:0.1, v/v/v) to (20:1:0.1, v/v/v), $CH_2Cl_2$/$CH_3CN$ (20:0.1, v/v) and with 20 and 50% $CH_3OH$ in $CH_2Cl_2$. TLC ($CH_2Cl_2$:$C_6H_{12}$:$CH_3CN$, 20:5:0.1, v/v/v) analysis showed the following fraction compositions: fractions 27–33 (A-1), $R_f$ 0.5, 8 mg; fractions 34–37 (A-2), 6 mg (mixture); fractions 38–49 (A-3), $R_f$ 0.3, 19 mg; fractions 64–135, (A04), $R_f$ 0.2, 42 mg; fractions 140–475 (A-5), a mixture of spots at $R_f$ 0.5, 0.15, 0.01 with ($CH_2Cl_2$:$C_6H_{12}$:$CH_3CN$ 20:2:0.5, v/v/v), 117 mg; and fractions 500 or higher (A-6), 487 mg (mixture). All fractions except (A-6) and late fractions which eluted with 20 and 50% $CH_3OH$ in $CH_2Cl_2$ appeared as white crystalline solids.

Sample Hydrolysis, Methylation, O-Trimethylsilylation for GC/MS Analysis

For hydrolysis and derivatization, samples of approximately 1 mg were dissolved in 2 mL of 5% methanolic KOH and refluxed for 10 h. Mixtures were evaporated to dryness under $N_2$, 2 mL of $H_2O$ was added to each residue, and the resulting aqueous mixtures were each extracted with $CH_2Cl_2$ (2×2 mL). Typically, this $CH_2Cl_2$ extract was dried over anhydrous $Na_2SO_4$ and evaporated to give 0.5 mg of neutral substances. The remaining aqueous phases were acidified with 2N HCl, extracted with $CH_2Cl_2$ (2×2 mL), dried over anhydrous $Na_2SO_4$ and evaporated to typically give 0.4 mg of acidic substances. These neutral and acidic substances were subjected to derivatization for GC/MS analysis.

a. Methylation: The acidic fraction after saponification was dissolved in 0.4 mL of HPLC grade $CH_3OH$, mixed with 1 mL $BF_3$—$CH_3OH$ and refluxed for 2–3 hours. The solvent was removed under N2, 1 mL of dis $H_2O$ was added, and the aqueous mixture was extracted with $CH_2Cl_2$ (2×1 mL). After drying over anhydrous $Na_2SO_4$, rotary evaporation gave methylated products for GC analysis or further derivatization with BSTFA.

b. O-Trimethylsilylation: This was accomplished by adding 35 µL of bis(trimethylsilyl)triflouroacetamide (BSTFA) to a solution of 0.7 mg of neutral substances obtained by saponification in 1 mL $CH_2Cl_2$, or 20 µL of BSTFA to a solution of 0.4 mg of methylated acidic compounds in 1 mL of $CH_2Cl_2$. The reactants were shaken for 20–30 minutes before samples were directly subjected to GC/MS analysis without further workup.

c. GC/MS Analysis: Gas chromatography (GC) was routinely performed with a Hewlett Packard 5890A gas chromatograph equipped with a fused silica capillary (SPB05) column, 30 m×0.32 mm ID, 0.20 µM film thickness, (Supelco Inc., Bellefonte, Pa.), and linked to a Hewlett Packard 3390A integrator. Nitrogen was used as carrier and make up gas at flows of 30 and 10 ml/min respectively, and eluting compounds were detected by flame ionization detection (FID). Column, injector and detector temperatures were maintained at 180°–210° C. (5° C./min), 220° and 300° C., respectively. Both column head carrier gas and hydrogen pressures were held at 35 psi. We used this method in evaluating the structures of hydroxy and oxo-fatty acids derived by the hydration and subsequent oxidation of oleic acid (El-Sharkawy et al., 1992). Low resolution mass spectra were obtained either by direct inlet probe sample admission, or by GC using methyl silicon (DB-1) column (50°–250°, 20° /min) in a Trio-1 mass spectrometer linked with a Hewlett-Packard 5890A Gas chromatograph.

Bioassays

Samples of 5–10 mg of extracts or chromatographic fractions were triturated into 50 mL of bovine plasma in a glass mortar. Samples were diluted with bovine plasma before being used in the placentome bioassay.

Placentomes were collected at a commercial slaughter facility from the gravid uterine horn of late pregnant cows between 240–270 days of gestation as determined by measurement of fetal crown rump length. (Evans and Jack, Prenatal Development of Domestic and Laboratory Mammals: growth curves, external features and selected references, *Anat. Histol. Embryol.* pp. 11–45, 1973). At the laboratory, placentomes were placed in an open perfusion chamber which was submerged in oxygenating Kreb's-Ringer solution and the caruncular artery was connected to polyethylene tubing, and the artery was gently perfused to remove blood from the vascular tree. The chamber was then sealed and a Harvard variable-speed peristaltic pump was used to deliver continuously oxygenated Kreb's-Ringer solution at 37° C. The extralumenal flow was maintained at 10 mL/min, and the instraluminal flow to each artery was maintained at 5 mL/min to achieve intraarterial pressures of approximately 80 mm Hg as measured by Statham pressure transducers and recorded on a Hewlett-Packard 7700 chart recorder. A pulse similar to that seen in the live animal was imposed on the intra-arterial flow with the use of a physiological perfusion pump (Medical Engineering Consultants, Los Angeles, Calif.). A ½ hr. equilibration period was allowed before the start of sample perfusion which allowed the placentome to establish a constant baseline perfusion pressure. Different Ponderosa pine needle extracts or chromatographic fractions dissolved in plasma were infused into the caruncular artery preparation at a rate of 0.5 mL/min with a Harvard dual syringe constant infusion pump (Conley and Ford, Effect of Prostaglandin $F_2\alpha$-Induced Luteolysis on In Vivo and In Vitro Progesterone Production by Individual Placentomes of Cows, *J. Anim. Sci.*, pp. 500–507, 1987). In general, two placentomes were perfused first for 20 min with vehicle, then samples with increasing concentrations of compounds or extracts for 20 min each, and then vehicle for 20 min. Vascular tone was estimated as the perfusion pressure established by the placentome preparation by the end of each 20 min perfusion period. At the end of each 20 min perfusion period (vehicle and samples) perfusion pressure was recorded, and a depolarizing bolus does of 0.2M KCl (200 µL) was injected into the intraluminal flow (5 mL/min) and increased perfusion pressure used to estimate the maximal potential sensitive calcium channel activity as previously described (Christenson et al., Effects of Pine Needles (*Pinus ponderosa*) by Late-Pregnant Beef Cows on Potential Sensitive $Ca^{2+}$ Channel Activity of Caruncular Arteries, *J. Reprod. Fertil.*, pp. 301–306, 1993). Each sample's vasoactivity was determined by by comparing the measurements of vascular tone and potential sensitive calcium channel activity at the end of its 20 min perfusion to baseline values. Baseline values were determined by averaging values at the end of both 20 min vehicle perfusion periods. Each sample was tested simultaneously in two placentomes on each experimental day and each sample was evaluated on at least 2 days.

Extraction and Isolation of Vasoactive Lipids

Steam distillation yielded a relatively small fraction (700 mg, 0.14% yield) of volatile oil. Acid and base partitioning of remaining suspensions of plant material led to complex extracts, none of which displayed biological activity in the placentome assay system.

For Soxhlet extraction, the best system involved sequential contacts with $Et_2O$, $CH_2Cl_2$ and $CH_3OH$ (Scheme 1) to obtain relatively large yields of pine needle extractables. $Et_2O$ removes relatively nonpolar substances in 8% (w/w) yield, $CH_2Cl_2$ gave 2.4% yield of a more polar fraction, while $CH_3OH$ gave 16% yield (w/w) of the most popular mixture of components. The total weight extracted represents 26.4% of the dry weight of the plant material used. In all preliminary placentome assays, $CH_2Cl_2$ extracts and chromatographic subfractions of the $CH_2Cl_2$ extracts were active in increasing PSC activity and vascular tone of the caruncular artery.

The *P. ponderosa* $CH_2Cl_2$ extracts were white, semicrystalline mixtures (TLC) of components. Aqueous acid and base partitioning of $CH_2Cl_2$ solutions of the extracts gave little indication of the possible presence of vasoactive acidic or basic components. Several different types of FCC purifications of this white material were attempted before successful fractionations were achieved. An apparently TLC pure ($R_f$ 0.7, with $CHCl_3/HCOOH$ [49:1]) vasoactive substance designated F7(1–10) was obtained upon initial FCC over silica gel. However, with another solvent system ($CH_2CL_2/C_6Hl_2/CH_3CN$, 20:5:0.1 v/v/v), this fraction was clearly a mixture of three spots migrating at $R_f$ 0.2, 0.5, and 0.7 which correspond to pure isolated spots later designated A-1, A-3 and an unknown material. Using the acetonitrile containing solvent system, fractions A1-A6 were obtained by FCC (Scheme 1) and subjected to bioassay in the placentome system.

Bioassay Results

The results of placentome bioassays on individual fractions and the mixture designated F7(1–10) are presented in Table 1. It was useful to examine the activity of the F7(1–10) mixture because of the possibility that mixtures of compounds could act synergistically or counteract each other in affecting potential sensitive calcium channel activity and tone with the placentome system. This sample gave significant increases in both perfusion pressure (tone) and in potential sensitive calcium channel activity when perfused through the placentome at 10 µg/mL. When diluted to 5 µg/ml, this sample exhibited little effect on tone, but the increase in potential sensitive calcium channel activity remained remarkably high (233%). At the lowest dose of 2.5 µg/mL, this fraction gave little response to either measures of vasoactivity.

Fraction A-1 appeared to cause dose-related increases in both tone and potential sensitive calcium channel activities of the vessels. Fraction A-3 increased primarily the KCl response, indicating a more specific effect on potential sensitive calcium channel activity. Neither fraction caused increases in vascular tone or potential sensitive calcium channel activity as high as those observed with F7(1–10). The results suggest that mixtures of compounds affect both the tone (i.e. vessel diameter) and potential sensitive calcium channel activity of the uterine vasculature, and that the effects of these compounds appear to be synergistic in nature. By spectral and chromatographic analysis, these samples contained no terpene acids such as isocupressic acid. Fractions A-4 and A-6 showed little activity, and samples A-2 and A-5 were not assayed because they were mixtures. The bioassay active fractions (A-1 and A-3) were subjected to spectral and chemical analysis.

TABLE 1

Vasoactivity evaluation of pine needle fractions in the placentome bioassay.

| Fraction | µg/mL Perfused | % Increase in BPP[a] at end of 20 min. | % Response to KCl above BPP[b] |
|---|---|---|---|
| F7(1–10) | 10 | 417 | 362 |
|  | 5 | 28 | 233 |
|  | 2.5 | 28 | 40 |
| A1 | 10 | 93 | 150 |
|  | 5 | 43 | 50 |
|  | 2.5 | 20 | 20 |
| A3 | 10 | 50 | 253 |
|  | 5 | 22 | 138 |
|  | 2.5 | 19 | 35 |
| A4 | 10 | 23 | 5 |
| A6 | 10 | 20 | 18 |

[a]BPP = Baseline perfusion pressure.
[b]Measure of potential sensitive calcium channel activity
A2 and A5 were not tested because they were mixtures.

LRFAB MS Analysis of Fraction F7(1–10)

Because fraction F7(1–10) was a complex mixture of substances, it was not subjected to complete spectral analysis. However, the LRFAB mass spectrum of this fraction in 3-NBA saturated with LiI is shown in FIG. 1. Prominent in this spectrum are the ions of m/z 573 (m/z 566+Li), m/z 601 (m/z 594+Li), m/z 629 (m/z 622+Li), and m/z 657 (m/z 650+Li). These ions are the primary components found in fraction A-1. Of lower intensities are ions of m/z 771 (m/z 764+Li), m/z 799 (m/z 792+Li), m/z 828 (m/z 821+Li) and m/z 856 (m/z 849+Li). These ions are the primary components found in fraction A-3. Those found in m/z 970, m/z 998, m/z 1026, m/z 1054 and m/z 1082 were the primary components in the bioassay inactive fraction A-4. From this spectrum it is apparent that there are at least four groups of similar components contained in F7(1–10). The relative amounts of these cannot be directly deduced from the relative intensities of molecular ions in the spectrum, because each group of compounds displays molecular ions of different intensities.

Spectral Analyses of Fraction A-1

Figure 2:
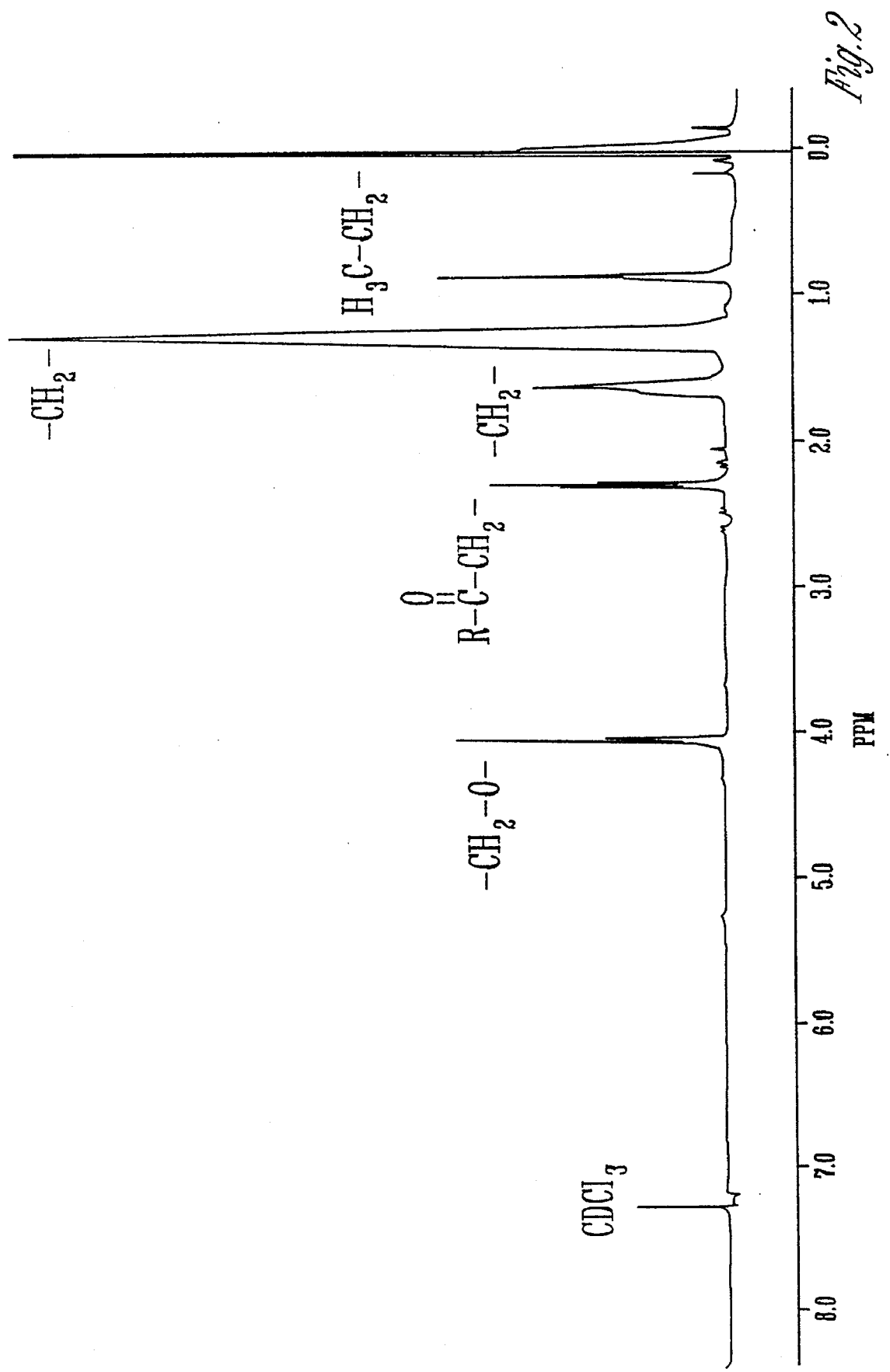
Figure 3:
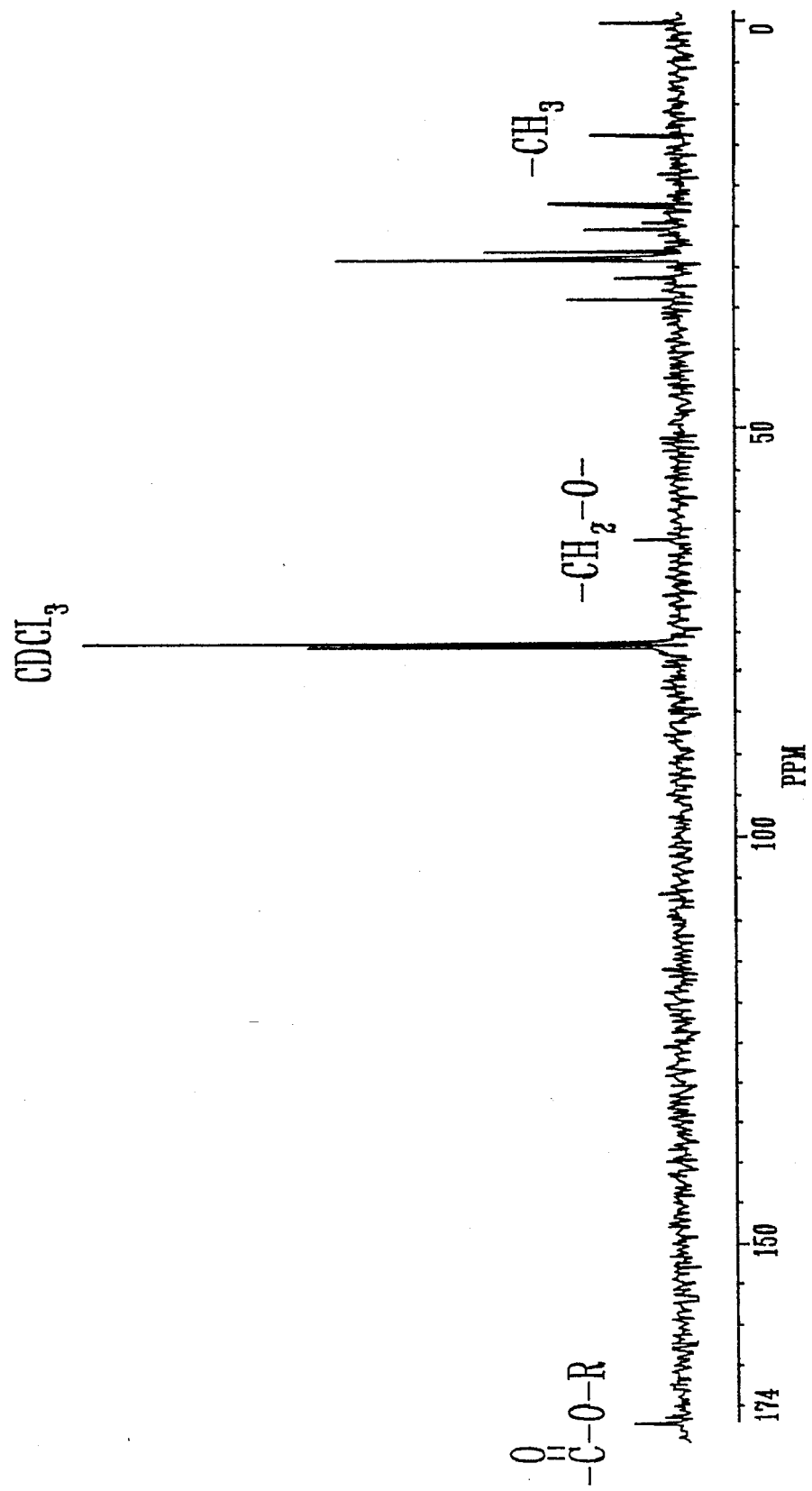

Fraction A-1 was apparently pure by TLC. Therefore, it was subjected to IR, 1H-and 13C-NMR and mass spectrometric analysis. The IR spectrum showed neither sharp nor broad bands between 3000–3600 cm–1, indicating the absence of free COOH or OH groups. A strong ester absorption band occurred at 1735 cm–1. 1H-NMR (FIG. 2) revealed signals typical for fatty acid esters with a 4-proton triplet at 4.05 ppm (—$CH_2OCO$—), a 4-proton triplet at 2.28 ppm (—$CH_2$—COO—), and 8-proton multiplet at 1.6 ppm (—$CH_2$—$CH_2$—COO—; and $CH_2$—$CH_2OCO$), a large 56-proton singlet at 1.26 ppm for numerous overlapping —$CH_2$— functional groups typical to those found in fatty acids, and a 6-proton triplet at 0.88 ppm representing terminal methyl groups. The 13C NMR spectrum (FIG. 3) exhibited signals for ester carbonyl carbons (174.02 ppm), ether carbons (64.38 ppm), and methyl carbons (14.12 ppm) together with numerous methylene-group carbon signals.

Figure 4:
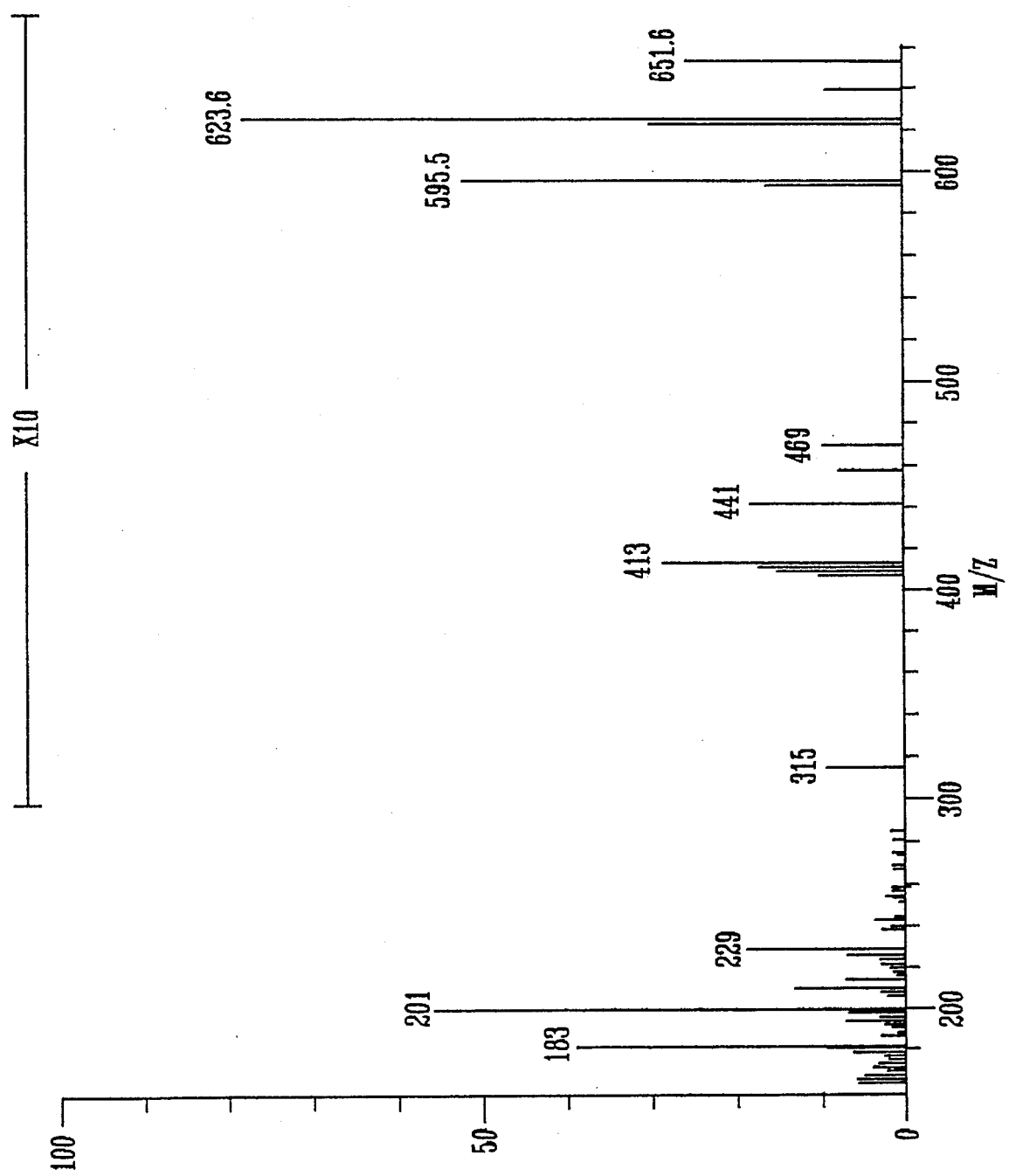

LRFAB MS with Magic Bullet as matrix (FIG. 4), indicated the presence of three major molecular ions of m/z 595.5 ($M_1$+H)$^+$, 623.5 ($M_2$+H)+ and 651.6 ($M_3$+H)$^+$. Confirming results were obtained by cationizing with lithium which resulted in (M+Li)$^+$ ions of m/z 601.5, and 629.6, and 657.5, respectively. These MS results indicated that the chromotographically pure material was actually a mixture of three major compounds and additional minor components. Assuming that relative intensities of the molecular ions reflected the actual concentrations of the three components in Fraction A-1, the major compound was that of m/z 623 (48%). Ions of m/z 595 and 651 represented 34% and 18% of Fraction A-1. The HRFAB analyses for ($M_1$+1)$^+$ and ($M_2$+1)+ ions resulted in masses of m/z 595.5674 which corresponds to an elemental composition of $C_{38}H_{75}O_4$ (theoretical 595.5665), and of m/z 623.5926 which corresponds to elemental composition of $C_{40}H_{79}O_4$ (theoretical 623.5977), respectively. The (M+H)$^+$ of m/z 651.6 can be regarded as possessing two additional methylene groups in its structure for $C_{42}H_{83}H_4$. Additional ions in the MS indicated that each of the maro components fragment and lose units of 182 u (dalton) which result in the formation of ions of m/z 413, 441 and 469, respectively. Another major fragmentation pathway produces low mass ions of m/z 183, 201, 211, and 229. HRFAB experiments have confirmed that ions of m/z 183 and 211 can be attributed to the acylium ions of lauric and myristic acid respectively. The identity of ions of m/z 201 and 229 was confirmed by HRFAB analyses to be protonated lauric and myristic acids, respectively. This MS data suggested the possibility that the structures of compounds contained in A-1 consisted of fatty acid diesters of alkanediols.

Tandem mass spectrometry experiments (MS-MS) were used to further analyze these compounds. MIKES scans were used to observe and characterize the unimolecular ion decompositions of the above (M+H)+ ions (AdaMS, Charge-remote fragmentations: Analytical applications and fundamental studies, *Mass Spectrom Rev.*, pp. 141–186, 1990; Jensen and Gross, 1987). The precursor ion of m/z 595.5 (FIG. 4) decomposed to produce ions of m/z 578 via loss of $H_2O$, m/z 413 via loss of 183 u or $C_{12}H_{23}O$, and m/z 395 via loss of 201 u or loss of $H_2O$ from the ion of m/z 413 ($C_{12}H_{25}O_2$). The low mass product ions include m/z 183, 195, and 201. The fragment ion of m/z 195 is thought to arise by loss of two dodecanoic (lauric) acid fragments from a tetradecanediol diester.

The parent ion at m/z 623.6 gave m/z 605 by loss of $H_2O$, m/z 441 by loss of an m/z 183 or $C_{12}H_{23}O$, m/z 423 by loss of an m/z 201 fragment or $C_{12}H_{23}O_2$, m/z 413 by loss of m/z 211 or $C_{14}H_{27}O$, 395 by loss of m/z 229 or $C_{14}H_{27}O_2$, and m/z 195 by loss of both dodecanoic (lauric) and tetradecanoic (myristic) acids from a tetradecanediol diester.

The precursor ion at m/z 651.6 gave a much more complex and noisy MS/MS spectrum indicating that this ion actually consisted of a mixture of different compounds possessing the same molecular mass. Useful information from this spectrum showed loss of $H_2O$ to give m/z 635, and subsequent fragmentations gave rise to numerous other ions as well. Losses of 183 u for $CH_3(CH_2)_{10}CO$ from lauric acid gave m/z 469; of 211 u for $CH_3(CH_2)_{12}CO$ from myristic acid gave m/z 441; and of 239 u for $CH_3(CH_2)_{14}CO$ from palmitic acid gave m/z 413. Ions at m/z 396, 422 and 450 can be explained by losses of palmitate ($CH_3(CH_2)_{14}COOH$, m/z 256), myristate ($CH_3(CH_2)_{12}COOH$, m/z 229) and laurate ($CH_3(CH_2)_{10}COOH$, m/z 200) from the molecular ion. At the lower end of the MS/MS spectrum, fragment ions for protonated palmitic acid (m/z 257), myristic acid (m/z 229) and lauric acid (m/z 201) were observed along with their accompanying m/z 239, 211 and 183 fragments, respectively. These results confirmed the presence of these three fatty acids as parts of the structures in the mixture giving rise to m/z 652. Noteworthy in this spectrum were the presence of two fragment ions at m/z 195 and 223 typical for ions arising from 1,14-tetradecanediol and 1,16-hexadecanediol, respectively.

Fraction A-1 was subjected to alkaline saponification in order to confirm the composition of presumed diesters contained in this mixture of lipids. Neutral and acidic fractions were trimethylsilylated and methylated and the derivatized components of A-1 were subjected to GC/MS comparisons with standard compounds (Eglington et al., Gas Chromotographic-Mass spectrometer Studies of Long Chain Hydroxy Acids-III, *Organic Mass Spectrometry*, pp. 593–611, 1968). Table 2 lists GC retention times and key fragments obtained for fatty acid methyl esters and trimethylsilylated alkanols and α,ω-alkanediol standards. From the total ion current chromatogram, and fragmentation patterns, the major neutral components were identified as 1,14-tetradecanediol and 1,16-hexadecanediol (FIG. 8). The acidic fraction (FIG. 7) contained methyl esters of lauric acid, myristic acid and palmitic acid in relative proportions of 1:4:1, and 1,14-tetradecanediol and 1,16-hexadecanediol in relative proportions of 4:6:1. Peaks with $R_T$ at 10.8 min are unknown artifacts that appeared in the GC chromatograms of both unknown and authentic standards derivatized in this work.

The results from MS and from hydrolysis and derivatization confirmed that the structures of compounds found in fraction A-1 are esters of lauric, myristic and/or palmitic acids esterfied with 1,14-tetradecanediol and/or 1,16-hexadecanediol. The MS/MS results confirmed the presence of 1,14-tetradecanediol-dilaurate(2) and 1,14-tetradecanediol- 1-laurate-14-myristic(3) for molecular ions at m/z 595 and 623. The ion at m/z 651 is a mixture of compounds of isomers. Based upon saponification and MS/MS analyses, there are only three possible combinations of fatty acid esters with alkanediols that match m/z 651. These are 1,14-tetradecanediol-dimyristate(4), 1,16-hexadecanedioyl-laurate-myristic(6) and 1,14-tetradecanediol-laurate-palmitate(5).

A separate isolation and analysis of A-1 yielded a mass spectrum slightly different than that originally seen for A-1. The major ions at m/z 595, 623, and 651 were evident albeit in different proportions than the previous A-1 fraction. A new ion at m/z 568 consistent for the structure 1,12-dodecanedioyl-dilaurate ($C_{36}H_{70}O_4$)(1) was observed. MS/MS of this ion gave m/z 550 ($C_{36}H_{68}O_3$) by loss of $H_2O$, m/z 385 by loss of m/z 183 or $C_{12}H_{23}O$, m/z 367 by loss of m/z 201 or $C_{12}H_{23}O_2$, and m/z 168 for $C_{12}H_{24}$ derived from 1,12-dodecanedioyl-dilaurate which eliminates the two ester fragments. This result confirmed the presence of the three compounds identified earlier in fraction A-1, and an additional derivative dodecanedioyl-dilaurate(1) in a second A-1 fraction. The results also underline the complexities in isolating mixtures of highly similar lipid substances from pine needle extracts. The structures of the compounds identified in the A-1 fraction are:

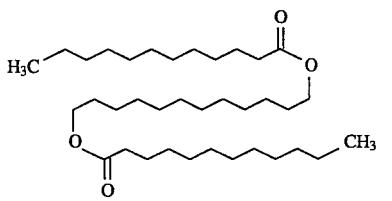

1

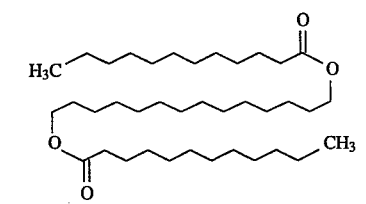

2

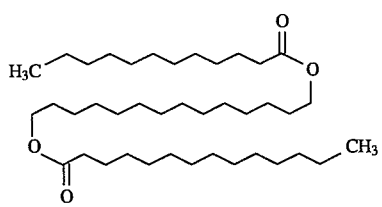

3

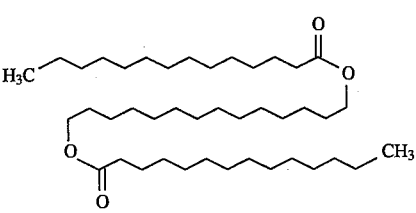

4

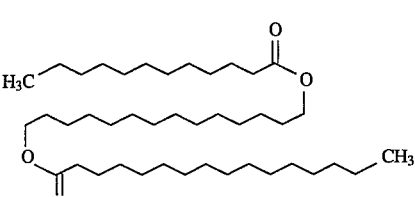

5

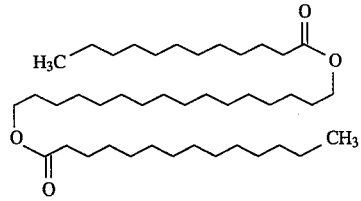

6

TABLE 2

GC-Retention times and key MS fragments of fatty acid methyl esters, trimethylsilylated alkanols, α, ω-alkanediols, and TMS-ω-hydroxyhexadecanoic acid methyl ester.

| COMPOUND | M/Z (M+) | GC-Retention time | Key MS Fragments M/Z |
|---|---|---|---|
| (Methyl Esters) | | | |
| Lauric(C-12) | 214 | 7.75 | 183, 74 |
| Myristic(C-14) | 242 | 8.98 | 211, 74 |
| Palmitic(C-16) | 270 | 10.11 | 239, 74 |
| (TMS Derivatives) | | | |
| Dodecan-1-ol | 258 | 8.12 | 243, 227, 185, 168, 75, 73 |
| Tetradecan-1-ol | 286 | 9.28 | 271, 255, 213, 196, 75, 73 |
| Hexadecan-1-ol | 314 | 10.35 | 299, 283, 224 75, 73 |
| Octadecan-1-ol | 342 | 11.34 | 327, 311, 75, 73 |
| 1,12-Dodecanediol | 346 | 10.05 | 315, 241, 75, 73 |
| 1,14-Tetradecanediol | 374 | 11.14 | 343, 284, 269, 75, 73 |
| (TMS, Methyl Ester) | | | |
| 16-Hydroxyhexadecanoic acid | 358 | 11.2 | 343, 284, 269, 75 |

Spectral Analysis of Fraction A-3

Figure 9:
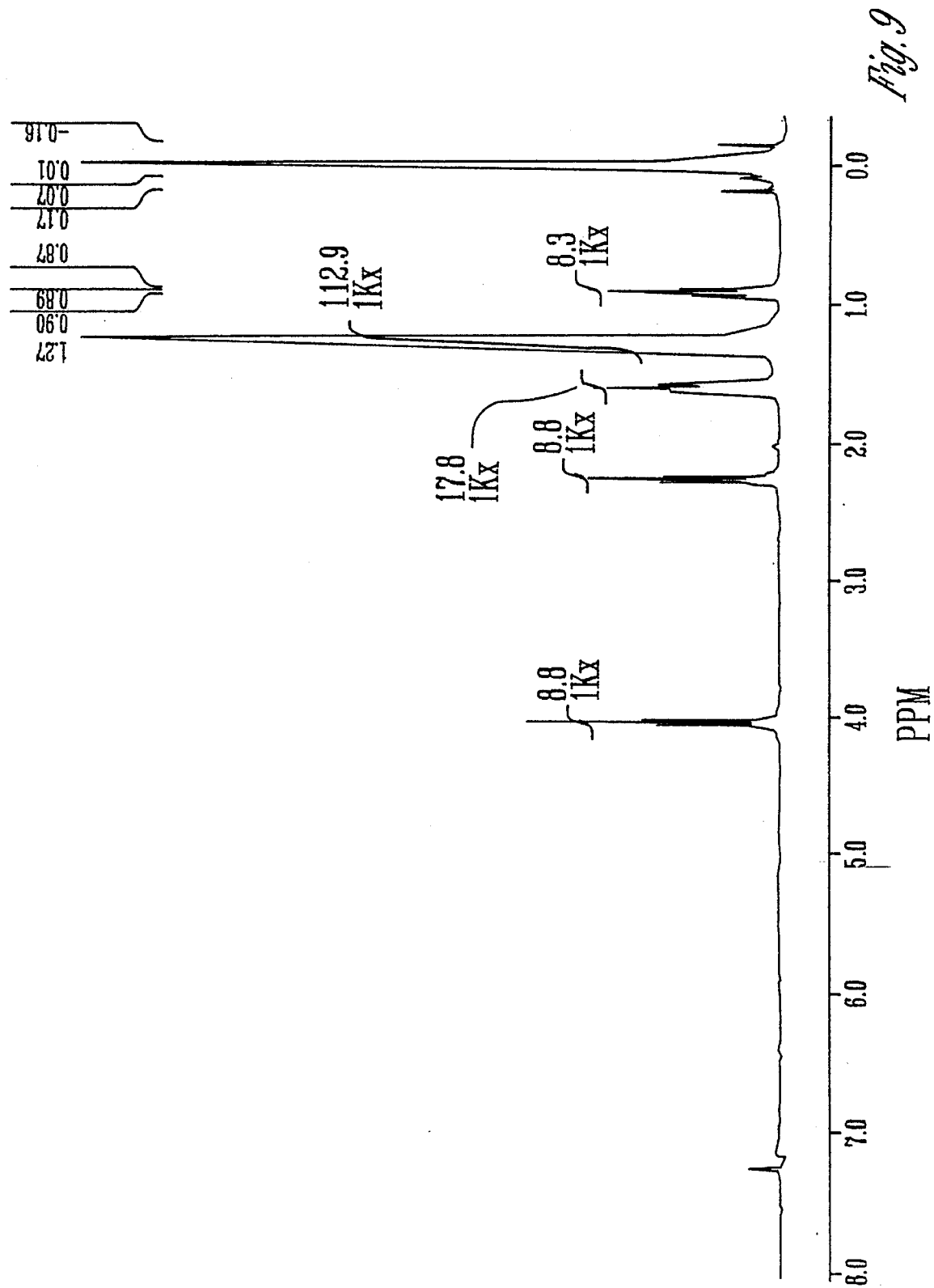
Figure 10:
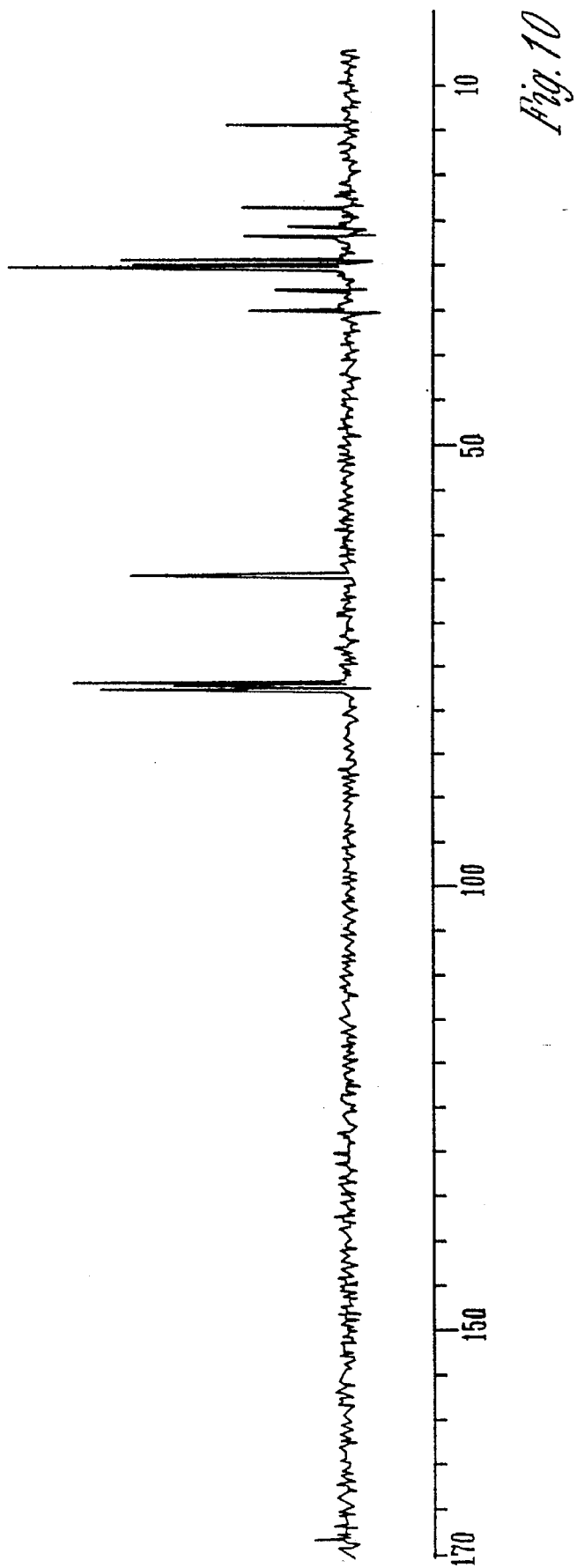

A-3 was the second chromatographically pure (TLC($CH_2Cl_2/C_6H_{12}/CH_3CN$ (20:5:0.1 v/v/v) fraction isolated from the $CH_2Cl_2$ pine needle extract (Scheme 1). This fraction was less active in elevating tone in the placentome assay (Table 1) but was considerably more active in elevating the KCl response. The infrared, 1H- (FIG. 9) and $^{13}C$-NMR (FIG. 10) spectra were essentially the same as for A-1. There were no free OH or COOH groups apparent and a prominent ester absorption band was observed. In the $^1H$-NMR spectrum, differences were found in the relative proton integrations for signals grouped at 4.05 ppm, 2.28 ppm, 1.60 ppm, 1.26 ppm and 0,88 ppm. Interestingly, the triplet signal at 0.88 ppm, which represents end-chain methyl groups, was smaller than it was in the $^1H$-NMR spectrum of A-1. The $^1H$-NMR spectrum also indicated that relatively simple and terminally oxygenated alkanes and fatty acids were likely components of fraction A-3. The $^1H$-NMR results would rule out the presence of 2° alcohols or ether functional groups in the components of this fraction. The $^{13}C$-NMR spectrum clearly indicated the presence of ester, numerous methylene, —O—$CH_2$—$CH_2$— and terminal methyl group signals like A-1.

Figure 11:
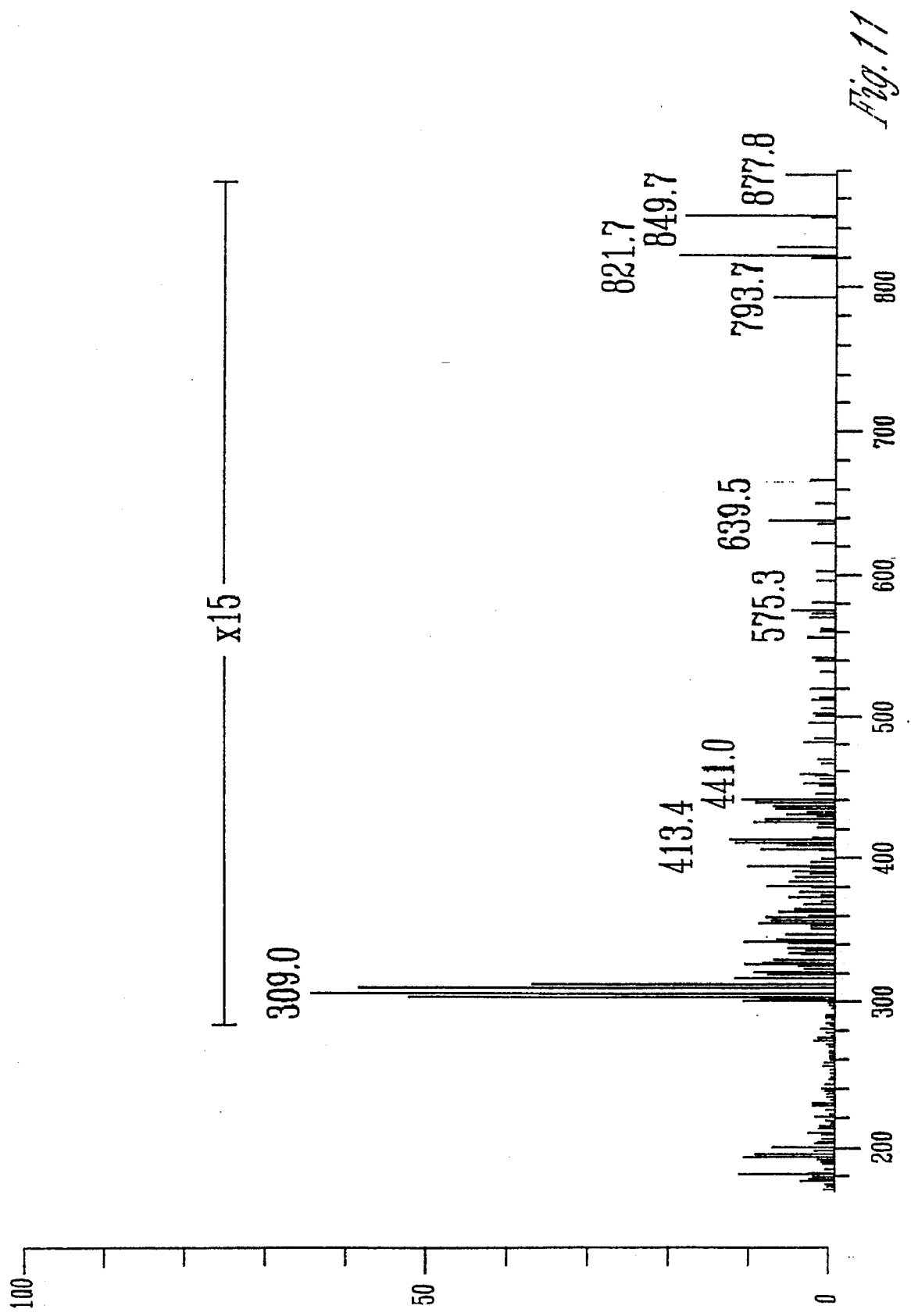

For A-3, LRFAB (Magic Bullet)(FIG. 11) gave ions of m/z 793.7 ($M_1$+H)+, 821.7 ($M_2$+H)+, 849.7($M_3$+H) and 877.8 ($M_4$+H)+. Mass spectral results indicated that A-3 was a mixture of at least four major compounds each apparently differing in mass by two $CH_2$— units from one another. HRFAB in 3-NBA (Magic Bullet) matrix gave m/z 821.7548 for $C_{52}H_{101}O_6(M+1)+$(theoretical 821.7597). This compound differs in mass by $C_{12}H_{22}O_2$ verses the major compound in fraction A-1 at m/z 623 for $C_{40}H_{79}O_4$ and identified as 1,14-tetradecanedioyl-laurate-myristate. The difference in structure can be explained by the presence of an ω-hydroxy fatty acid.

Saponification of A-3 and GC/MS of the resulting O-trimethylsilylated neutral $CH_2Cl_2$ extract indicated that 1,14-tetradecanediol-di-O-TMS was the major (90%) neutral component with about 10% of 1,16-hexadecanediol-1-O-TMS. These results were identical to those obtained with authentic compounds, and seen earlier with fraction A-1 (FIG. 7). The acidic extract of A-3 gave total ion chromatogram peaks and fragmentation patterns consistent with the presence of methyl myristate, methyl palmitate, O-trimethylsilyl-ω-OH-hexadecanoic acid methyl ester, 1,14-tetradecanediol-di-O-TMS, and 1,16-hexadecanediol-1-O-TMS (Table 2). The major difference in the acidic fraction of $A_3$ was the presence of a major peak (@90% of acids)($T_R$ 11.2 min) matching with the O-TMS derivative of 16-hydroxy-hexadecanoic acid methyl ester with ions of m/z 343=(M-15), 284=(M-74), 269=(M-15-74), 75, 74 and 73.

MS data and derivatization of saponified samples suggest the presence of much more complex components within the A-3 mixture of compounds. The major diol is 1,14-tetradecanediol, and palmitic and myristic acids appear to be common fatty acid components of compounds in A-3. The presence of ω-hydroxy-hexadecanoic acid (16-hydroxypalmitic acid) suggests that the structures of esters found in A-3 are comprised of two fatty acids esterfied together with one alkanediol and one ω-hydroxy fatty acid. We suggest the structures of compounds 7–11, previously shown, that fit the MS and chemical derivatization GC/MS data. The compound with m/z 821 is represented as structure 10 for $C_{52}H_{101}O_6$. In all but the compound with the lowest mass at m/z 792, ω-hydroxypalmitic acid (16-hydroxyhexadecanoic acid) exists as the hydroxy-fatty acid component of the esters. In order to obtain m/z 792, 14-hydroxytetradecanoic acid replaces 16-hydroxyhexadecanoic acid shown in all other structures, even though direct evidence for its presence in saponified samples was not seen. Compounds with m/z 876 can be represented by more than one isomeric form such as 7 or 8. Attempts to derive confirming information by MS/MS analysis of peaks for fraction A-3 were unsuccessful.

This work describes new structural classes of vasoactive lipids dominated by the presence of alkanediols esterified with myristic and/or lauric acids. The fact that components of A1 and A3 appear to have differential effect on vascular tone and potential sensitive calcium channel activity suggests that reductions in blood flow in vitro and perhaps in vivo may be due to the presence of structurally similar compounds with two types of vasoactivity.

As shown above, several of the new compounds isolated by Applicants demonstrated ability in increasing the perfusion pressure in placentome bioassays. The components present in the F7(1–10) fraction, which contain compounds present in both the A1 and A3 fractions, caused the highest increase in both vascular tone and potential sensitive calcium channel activity, suggesting that the A1 and A3 fractions produce synergistic effects when used in combination. The isocupressic acid component previously isolated by James et al. was not present in any of these fractions.

Therefore it has been demonstrated that the invention disclosed above accomplishes at least all of its stated objectives.

In the specification there has been set forth examples which are not meant to limit the invention in any manner but are provided for demonstrative purposes only.

What is claimed is:

1. A method of increasing the perfusion pressure of caruncular arterial beds in mammals, comprising: administering a small, but perfusion pressure-increasing, amount of a substantially pure esterified fatty acid, wherein the fatty acid is selected from the group consisting of lauric, myristic and palmitic acid.

2. The method of claim 1 wherein the fatty acid is esterified with an alkanediol.

3. The method of claim 1 wherein the alkanediol is 1,14-tetradecanediol.

4. The method of claim 1 wherein the alkanediol is 1,16-hexadecanediol.

5. The method of claim 1 wherein the esterified fatty acid is selected from the group consisting of:

1,14-tetradecanedioyl-dilaurate;

1,14-tetradecanedioyl-1-laurate-14-myristate;

1,14-tetradecanedioyl-dimyristate;

1,16-hexadecanedioyl-laurate-myristate; and 1,14-tetradecanedioyl-laurate-palmitate.

6. The method of claim 1 wherein the esterified fatty acid is 1,12-dodecanedioyl-dilaurate.

7. The method of claim 1 wherein the esterified fatty acid is selected from the group consisting of:

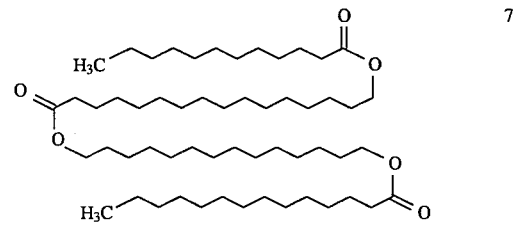

7

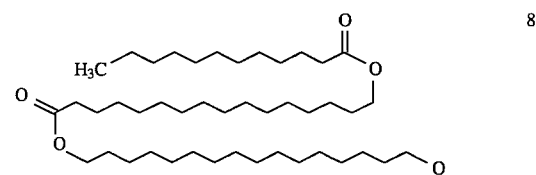

8

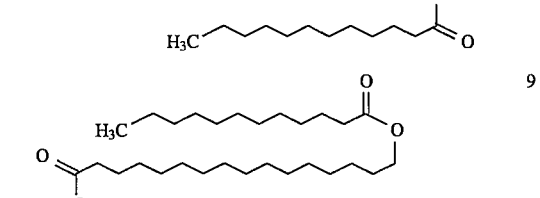

9

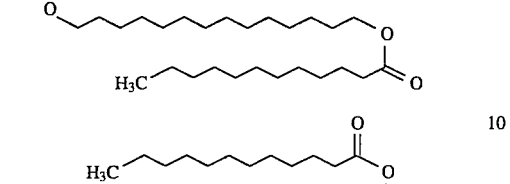

10

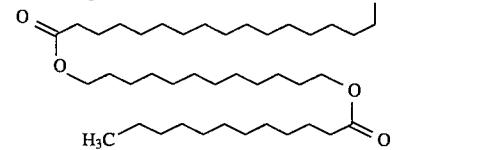

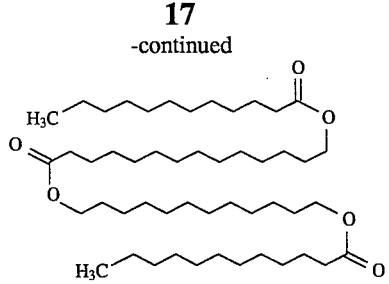

8. The method of claim 5 wherein the dose is ½ to 1.5 mg/kg of body weight/day, orally for 8–10 days.

9. The method of claim 8 wherein the dose is 1.5 mg/kg of body weight/day, orally, for 10 days.

10. A method of increasing the perfusion pressure of caruncular arterial beds in mammals, comprising: administering a small, but perfusion pressure-increasing, amount of a substantially pure fatty acid esterified with a compound selected from the group consisting of 1,14-tetradecanedioyl, 1,12-dodecanedioyl, and 1,16-hexadecanedioyl, wherein said fatty acid is selected from the group consisting of lauric, myristic, and palmitic acid.

11. A method of increasing the perfusion pressure of caruncular arterial beds in mammals, comprising:
administering a small, but perfusion pressure-increasing, amount of a substantially pure esterified fatty acid selected from the group consisting of:
1,14-tetradecanedioyl-dilaurate;
1,14-tetradecanedioyl-1-laurate-14-myristate;
1,14-tetradecanedioyl-dimyristate;
1,16-hexadecanedioyl-laurate-myristate;
1,14-tetradecanedioyl-laurate-palmitate;
1,12-dodecanedioyl-dilaurate;
1-(16-laurylatepalmitate)-14-myristate-tetradecanediol;
1-(16-laurylatepalmitate)-16-laurate-hexadecanediol;
1-(16-laurylatepalmitate)-14-laurate-tetradecanediol;
1-(16-laurylatepalmitate)-12-laurate-dodecanediol; and
1-(14-laurylatemyristate)-12-laurate-dodecanediol or combinations thereof.

* * * * *